United States Patent [19]

Parmigiani

[11] Patent Number: 5,533,984
[45] Date of Patent: Jul. 9, 1996

[54] PROTECTION DEVICE FOR A BODY-PENETRATING SYRINGE NEEDLE

[75] Inventor: Corrado Jr Parmigiani, Correggio, Italy

[73] Assignee: C.G.M. S.P.A., Reggio Emilia, Italy

[21] Appl. No.: 490,528

[22] Filed: Jun. 14, 1995

[30] Foreign Application Priority Data

Jun. 23, 1994 [IT] Italy ................................. RE94A0047

[51] Int. Cl.⁶ .................................................. A61M 5/32
[52] U.S. Cl. ......................... 604/263; 604/162; 604/192
[58] Field of Search .................................... 604/263, 192, 604/187, 162, 177

[56] References Cited

U.S. PATENT DOCUMENTS

| | | | |
|---|---|---|---|
| 3,574,306 | 4/1971 | Alden | 604/162 |
| 4,758,229 | 7/1988 | Doerschner | 604/187 |
| 4,875,896 | 10/1989 | Kurtz | 604/187 |
| 4,888,001 | 12/1989 | Schoenberg | 604/162 |

FOREIGN PATENT DOCUMENTS 1447237   8/1976   United Kingdom ............... 604/162

*Primary Examiner*—John D. Yasko
*Attorney, Agent, or Firm*—Birch, Stewart, Kolasch & Birch

[57] ABSTRACT

A plate-like front element (20) is provided adjacent but not constrained to the needle tube (11) and foldable on itself about a first folding axis (A) parallel and close to the tube A. A rear element (30) is also provided for constraining the needle support member (12) to the front element (20) such that this can be rotated about a second folding axis (B) transverse to the axis of the tube (11). The device can assume a first operating configuration in which the element (20) is folded on itself about the first axis (A) with the front portion of the tube (11) enclosed between the two fins (21, 22) of the element (20). The device can assume a second operating configuration in which, by rotating the front element (20) about the second axis (B), the tube (11) projects forwards of the front element (20).

12 Claims, 3 Drawing Sheets

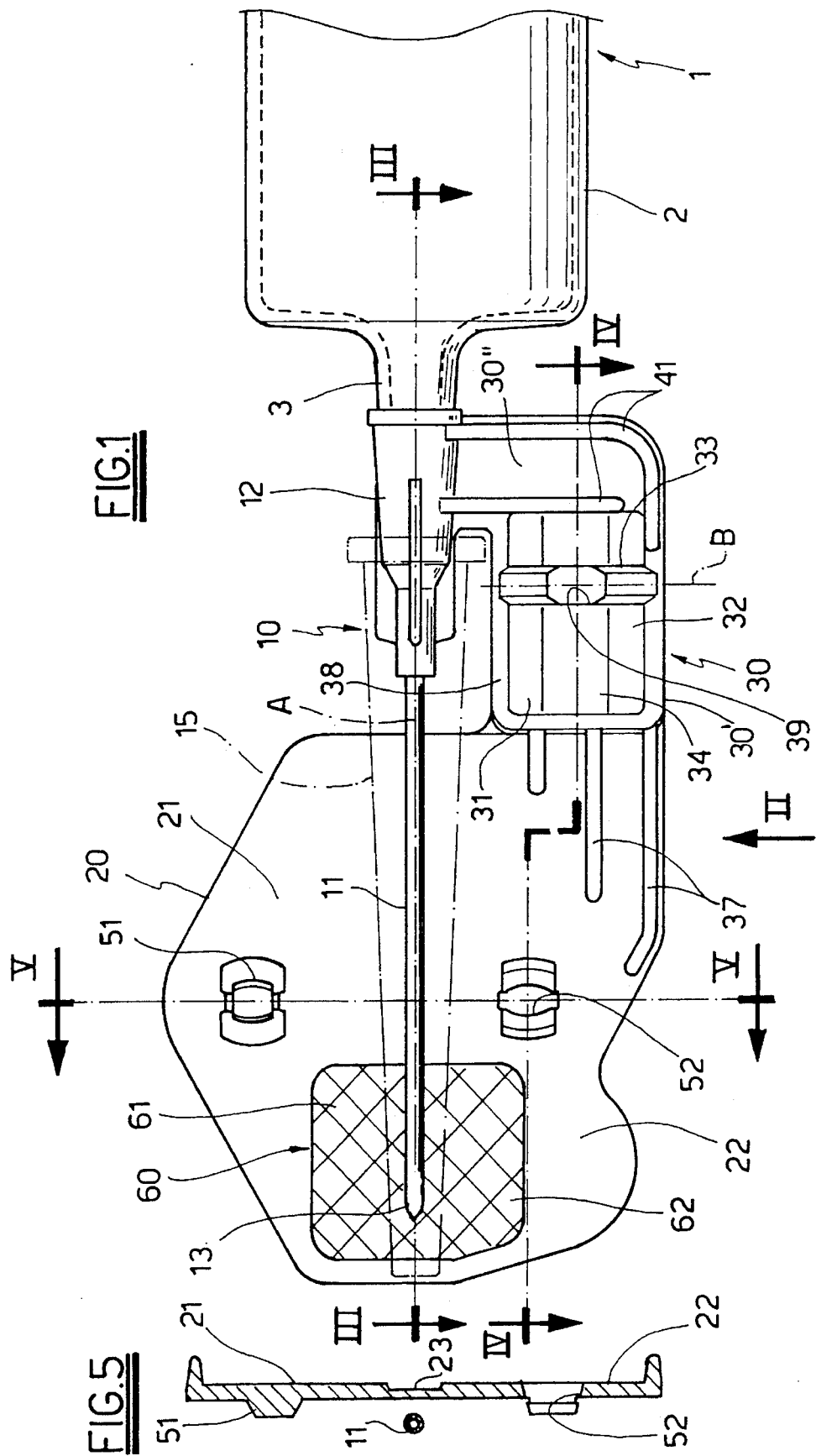

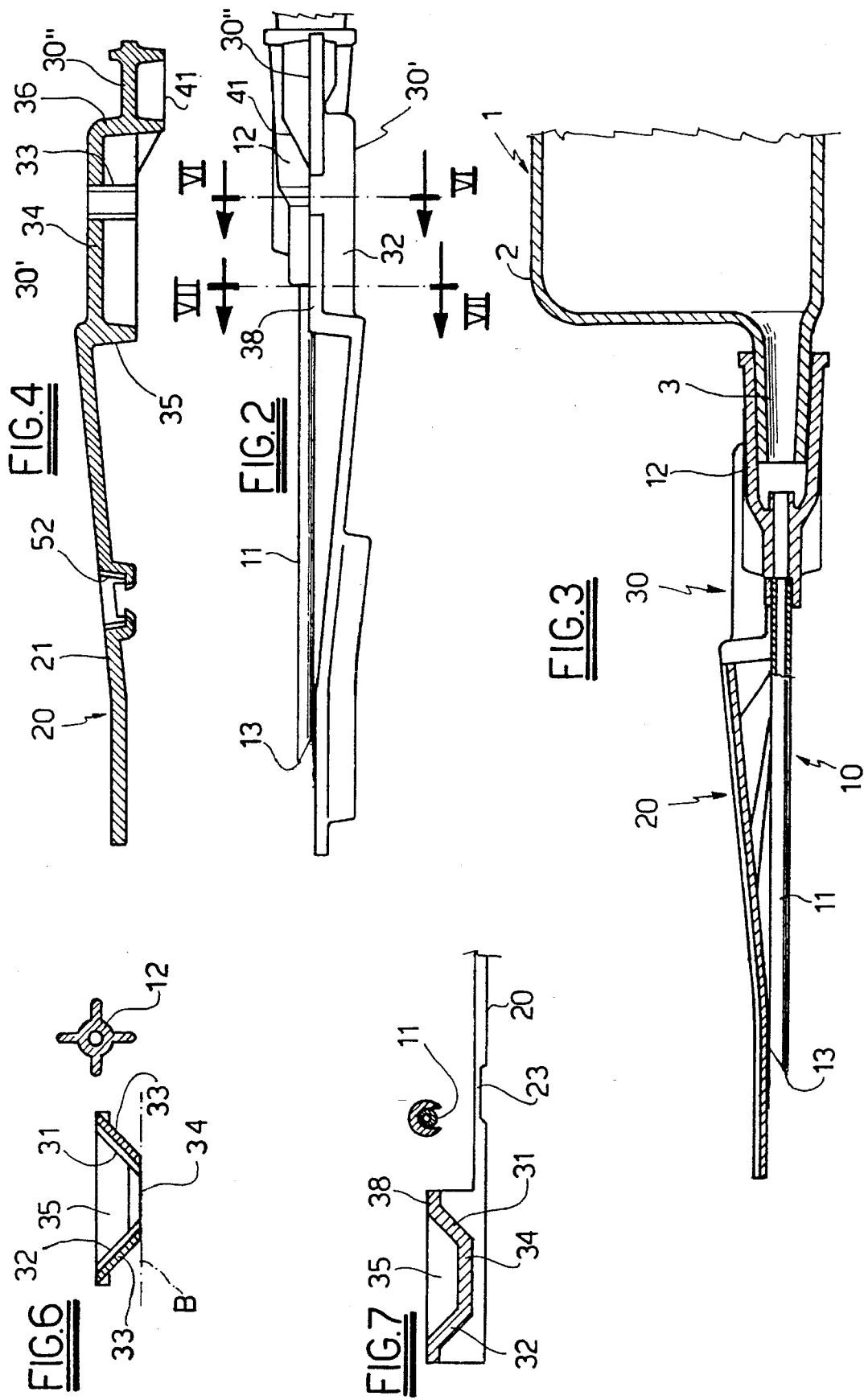

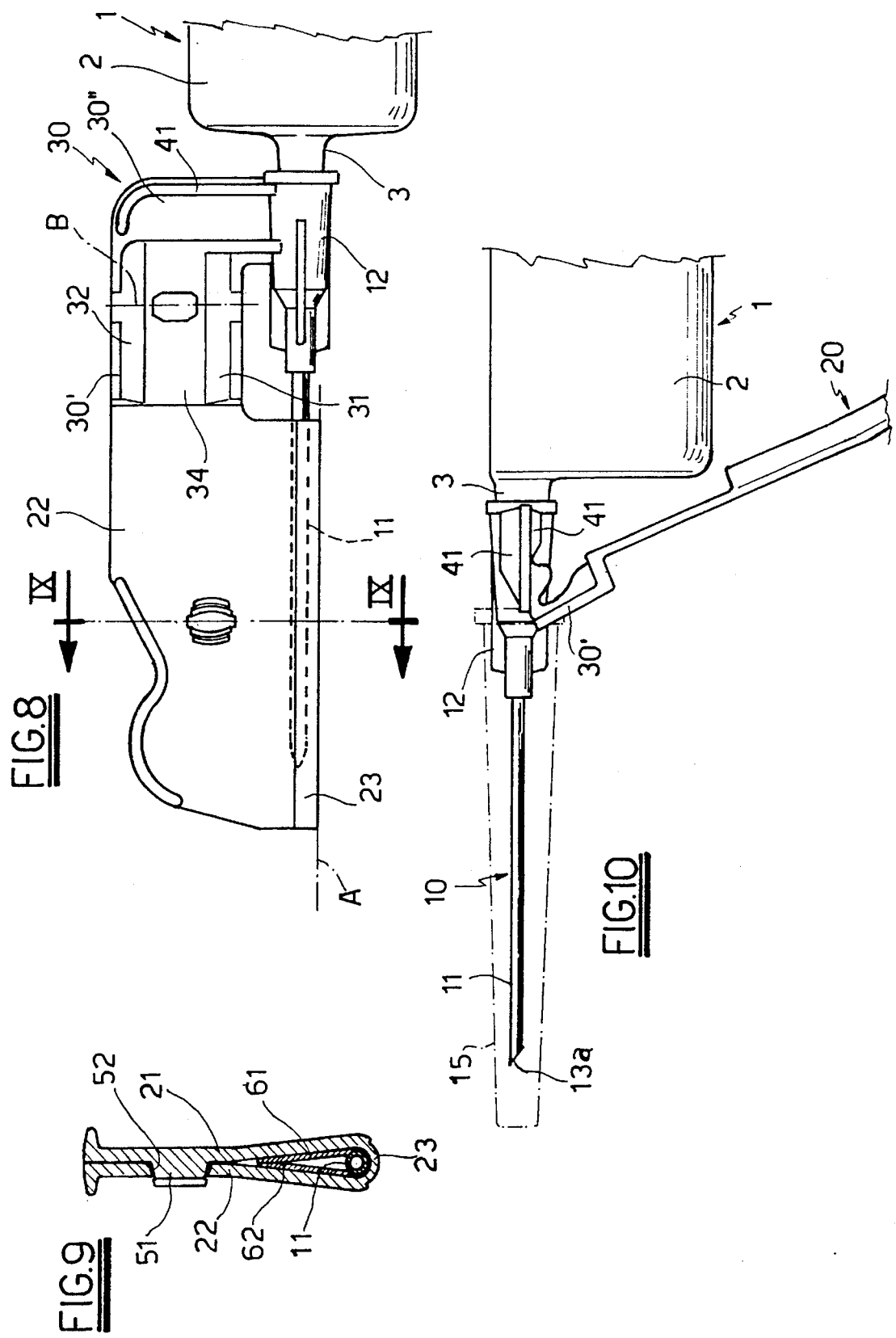

5,533,984

PROTECTION DEVICE FOR A BODY-PENETRATING SYRINGE NEEDLE

FIELD OF THE INVENTION

This invention relates to syringe needles for body penetration, both for introducing liquid substances and for extracting blood for example.

DESCRIPTION OF THE BACKGROUND ART

Said needles are known to usually comprise a pointed metal tube joined to a hollow support member which is fixed to the cylindrical body of the syringe. The present invention confronts the problem of protection against pricking by needles especially after they have been inserted into a patient's body. In this respect, if needles prick or scratch a second person after they have been used on a first person, they can become a transmission vehicle for diseases. There is therefore a considerable danger connected with the handling of these needles especially by those who usually work with them, in particular hospital staff. The disposal of used needles as refuse also creates danger for those who handle the refuse containers or who approach such containers. For these reasons it has become usual, after their use, to cover the point of such needles by remounting on them the cap which is used to protect the needle before use. However, mounting said cap on the needle is an operation which requires a certain precision and has also resulted in pricking. A further drawback is that when the cap is removed from the needle it can easily become lost, being of relatively small dimensions.

SUMMARY OF THE INVENTION

The object of the present invention is to obviate said drawbacks within the framework of an economical and effective construction.

This object is attained by the device of the invention as characterised in the claims.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention is described in detail hereinafter with the aid of the accompanying figures, which are given by way of illustration only, and thus are not limitative of the present invention, and which illustrate one embodiment thereof.

FIG. 1 is an enlarged plan view of a first embodiment of the invention in the extended configuration.

FIG. 2 is a side view in the direction of the arrow II of FIG. 1.

FIG. 3 is a section on the plane III—III of FIG. 1.

FIG. 4 is a section on the plane IV—IV of FIG. 1.

FIG. 5 is a section on the plane V—V of FIG. 1.

FIG. 6 is a section on the plane VI—VI of FIG. 2.

FIG. 7 is a section on the plane VII—VII of FIG. 2.

FIG. 8 is a plan view of the device in its first operating configuration, taken from the opposite side to that of FIG. 1.

FIG. 9 is a section on the plane IX—IX of FIG. 8.

FIG. 10 is a view similar to that of FIG. 2, showing the device in its second operating configuration.

DETAILED DESCRIPTION OF THE PREFERRED EMBODIMENTS

The body-penetrating needle is indicated overall by 10 in the figures. It comprises a thin tube 11 with a point 13 and fixed to a hollow support member 12 of substantially known shape, to be joined to a syringe 1 of known type, in particular by inserting it under pressure into a short tube 3 projecting from the cylindrical body 2 of the syringe. A usual plunger or other means (not shown in the figures) slides within the body 2 to inject/withdraw liquid substances, blood, etc.

The device of the invention comprises a substantially flat front element 20 positioned adjacent but not constrained to the tube 11.

The element 20 is foldable on itself substantially about a first folding axis A parallel and relatively close to the tube 11.

The device also comprises a means (described in detail hereinafter) for constraining the support member 12 to the front element 20 such that the element 20 can be rotated substantially about a second folding axis B substantially transverse to the axis of the tube 11.

The term "folding axis" means either a true axis of rotation about which two rigid bodies rotate (in the case of two rigid bodies articulatedly connected together) or a folding region along which a body deforms by flexure (in the case of a single flexible body).

The device of the invention can assume a first operating configuration (illustrated in FIGS. 8 and 9) in which the element 20 is folded on itself by rotation about the first axis A, such that its two fins 21 and 22 face each other in mutual contact, and with the front portion of the tube 11 enclosed between the two fins 21 and 22. The point 13 of the needle does not project from the element 20.

The device of the invention can also assume a second operating configuration (FIG. 10) in which, by rotating the front element 20 relative to the needle 10 about the second axis B, the tube 11 projects freely forwards from the front element 20. The front element 20 is sufficiently rigid such that in normal use (for example if struck on its edge by any part of the operator's body) it cannot undergo deformation such as to enable the point 13 of the needle to project beyond the element 20 when folded into its first configuration.

Preferably the front element 20 is in the form of a relatively thin substantially flat plate and possesses a reduced-thickness folding region 23 which represents the first folding axis A.

Said constraining means comprises a relatively rigid rear element 30, firmly joined to the rear side of the element 10 and to the support member 12, and extending substantially to the side of the member 12. The rear element 30 has a reduced-thickness folding region 33 defining the second axis of rotation B. Preferably, the rear element 30 is overall of substantially flat shape coplanar with the front element 20.

The front element 20, the rear element 30 and the support member 12 are preferably formed as a single synthetic resin body of sufficient elastic flexibility.

The rear element 30 has a portion 30' roughly of trough shape (ie in the form of a trapezium-based prism open on a lateral face). Specifically, the portion 30' has two walls 31 and 32 lying in planes which converge into an ideal straight line of intersection parallel to the tube 11 and are slightly inclined to the general plane of the front element 20. The two walls 31 and 32 are connected together by a peripheral rim 38, defining the mouth of the trough, by a base wall 34 and by frontal ribs 35 and 36. Further ribs 37, parallel to the tube 11, stiffen that region of the element 20 joined to the element 30.

The portion 30 is joined to a second flat rear portion 30" joined to the support member 12. Ribs 41 stiffen the portion 30".

The folding region 33 extends along the inclined walls 31 and 32 in a manner transverse to said ideal straight line of intersection of the wall planes. This folding region comprises a hole in correspondence with the base wall 34.

The particular form of the portion 30' (ie of the walls 31 and 32 and their constituent material) gives rise to an elastic means which tends to maintain the second operating configuration stable. When the element 20 is rotated into the second configuration, the portion 30' is folded on itself about the region 33, the particular trough shape meaning that this rotation firstly puts the walls 31 and 32 under tension (in particular those wall portions involving the region 33), hence requiring a small force for the rotation action. After passing beyond 90°, the said material of the walls 31 and 32 tends, by elastic reaction, to increase the folding angle. Hence she element 20 snaps into its folded position, this configuration (FIG. 10) being maintained stable.

Means are also provided on the front element 20 for retaining together the two mutually facing fins 21 and 22 when positioned in the first configuration. These retention means comprise one or more projections 51 provided on the fin 21 and one or more corresponding cavities 52 provided in the other fin 22. The projection 51 is able to snap-insert into the cavity 52 to create a sufficiently secure constraint.

On the inner surface of the front element 20 (ie inner when the element 20 is in the first configuration) there can be provided an elastically soft layer 60 positioned in correspondence at least with the final portion of the tube 11, in order, when the element 20 is folded on itself into the first configuration, to press against the final portion of the tube, in particular on the point 13, to surround it and close its mouth 13a.

Preferably, the soft layer 60 is formed of expanded synthetic resin of closed-cell type.

Specifically, the soft layer 60 is positioned on the front part of the element 20, straddling the folding region 23, so that it possesses two portions 61 and 62 arranged on one and the other side of the axis A, to be pressed against one another when in the first configuration, with the final portion of the tube 11 interposed between them.

Before use, during the distribution of the product, the tube 11 is covered with a usual rigid cap 15 (shown by dashed and dotted lines in FIGS. 1 and 10) the mouth of which is mounted with slight pressure on the support member 12, in the usual manner.

To arrange the needle for insertion into the patient's body, after the needle has been connected to the syringe 1 (which can also be done before distribution), the element is firstly rotated with one finger about the axis B to bring it into the second operating configuration (FIG. 10). This operation carries no danger of pricking because the tube 11 is covered with the cap 15.

The cap 15 is then removed so that the tube 11 projects freely forwards of the syringe 1 and is not hindered by the element 20 as this has been folded backwards against the front face of the cylindrical body 2 of the syringe (FIG. 10).

When in this configuration the syringe and needle can be handled in the usual manner for inserting the needle into the patient's body.

After the needle has been extracted from the patient, the element 10 is again rotated with one finger about the axis B and moved to the side of the tube 11. The elastic reaction provided by the portion 30' facilitates this rotation in that, on exceeding an angle of 90°, the element 20 snaps automatically to the side of the tube 11. After this, the fin 21 is rotated about the axis A relative to the other fin 22, with consequent folding of the element 20 on itself, so that the element 20 is brought into the first operating configuration in which the two fins 21 and 22 are retained by snap-inserting the projection 51 into the cavity 52. This operation is also carried out without danger of pricking the operator's band because the fingers act on that surface of the element 20 facing the opposite side to that on which the tube 11 lies.

When in this configuration, the point 13 of the needle is enclosed between the fins 21 and 22 and hence cannot produce pricking.

In addition, the layer 60 encloses the final portion of the tube 11 and in particular the mouth 13a. Consequently any blood present in the tube 11 cannot escape therefrom because the mouth 13a is sealed by the layer 60. The blood present on the outer surface of the tube 11 is also enclosed by the layer 60 and hence cannot come into contact with the person. Hence without any danger of infection etc., the needle 10 together with the protection device can be separated from the syringe 1 and be disposed of in suitable containers, or can be disposed of together with the syringe itself, to be scrapped without any danger to the person as it is protected by the device.

Numerous modifications of a practical and applicational nature can obviously be made to the invention, and in particular the geometrical form of the illustrated protection device can be changed.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

I claim:

1. A device for protecting a body-penetrating syringe needle, said needle having a tube fixed to a hollow support member connectable to a cylindrical body of the syringe, the device comprising:

a plate-like front element provided adjacent but not constrained to the needle tube and foldable on itself substantially about a first folding axis substantially parallel and relatively close to the tube, the front element having two fins; and means for constraining the needle support member to said front element such that the front element is rotatable substantially about a second folding axis transverse to a longitudinal axis of the tube;

the device being able to assume a first operating configuration in which the front element is folded on itself about the first axis with the two fins mutually facing and in contact with each other and with the front portion of the tube enclosed between the two fins, a point of the needle not projecting from being enclosed by the front element;

the device being able to assume a second operating configuration in which, by rotating the front element relative to the needle about said second axis, the tube projects forward of said front element;

the front element being sufficiently rigid to avoid deformation during normal use of the needle which would result in the point of the needle projecting externally from the element when the device is in the first operating configuration.

2. The device as claimed in claim 1, wherein said front element is in the form of a relatively thin substantially flat plate having a reduced-thickness folding region which defines the first axis of rotation.

3. The device as claimed in claim 1, wherein said constraint means comprises a rear element rigidly joined to a rear side of the front element and to the needle support member and extending to the side of the member, said rear element having a reduced-thickness folding region which defines the second axis of rotation.

4. The device as claimed in claim 3, wherein said rear element comprises a portion shaped to define an elastic means which tends to maintain the position of the front element stable when in the second operating configuration.

5. The device as claimed in claim 4, wherein said portion comprises two walls which if extended converge into a generally straight line of intersection, the two walls being slightly inclined to a general plane of the front element, a second folding region extending along said inclined walls transversely to the straight line of intersection, said walls because of their geometrical form and the elasticity of the material, providing elastic means which tends to maintain the second operating configuration stable.

6. The device as claimed in claim 4, wherein said rear element is overall of substantially flat shape and is coplanar with the front element.

7. The device as claimed in claim 1, further comprising means for retaining together the two mutually facing fins of the front element when positioned in the first operating configuration.

8. The device as claimed in claim 7, wherein said means for retaining comprise a projection on one fin arranged to snap-insert, under pressure, into a corresponding cavity provided in a facing position in the other fin.

9. The device as claimed in claim 1, wherein the front element, the constraint means and the needle support member are provided as a single body of synthetic resin.

10. The device as claimed in claim 1, further comprising an elastically soft layer applied to an inner surface of the front element in correspondence at least with an end portion of the tube, said soft layer being arranged, when the front element is folded on itself into the first operating configuration, to press against the end portion of the tube, in order to surround the end portion of the tube and to close a mouth of the point of the needle.

11. The device as claimed in claim 10, wherein said soft layer comprises two portions arranged on one and the other side of the first folding axis, the two portions of the soft layer are pressable against one another when in said operating configuration, with the final portion of the tube being interposed therebetween.

12. The device as claimed in claim 10, wherein said soft layer is formed of closed-cell, expanded synthetic resin.

* * * * *